(12) United States Patent
Massengill et al.

(10) Patent No.: US 10,463,784 B2
(45) Date of Patent: Nov. 5, 2019

(54) MOBILE MOUNTING STRUCTURE FOR MEDICAL EQUIPMENT

(71) Applicant: BSTR, LLC, Zebulon, NC (US)

(72) Inventors: Brandon Massengill, Zebulon, NC (US); Spencer Rocco, Greenville, NC (US); Timothy Boone Berlin, Goose Creek, SC (US); Ron Mitchell, Apex, NC (US)

(73) Assignee: BSTR, LLC, Raleigh, NC (US)

( * ) Notice: Subject to any disclaimer, the term of this patent is extended or adjusted under 35 U.S.C. 154(b) by 0 days.

(21) Appl. No.: 15/567,739

(22) PCT Filed: Apr. 22, 2016

(86) PCT No.: PCT/US2016/029061
§ 371 (c)(1),
(2) Date: Oct. 19, 2017

(87) PCT Pub. No.: WO2016/172638
PCT Pub. Date: Oct. 27, 2016

(65) Prior Publication Data
US 2018/0154071 A1  Jun. 7, 2018

Related U.S. Application Data

(60) Provisional application No. 62/151,430, filed on Apr. 23, 2015.

(51) Int. Cl.
*A61M 5/14* (2006.01)
*A61G 7/05* (2006.01)

(52) U.S. Cl.
CPC ......... *A61M 5/1415* (2013.01); *A61G 7/0503* (2013.01); *A61M 2209/084* (2013.01)

(58) Field of Classification Search
CPC ... A61M 5/00; A61M 5/14; E04G 3/00; F16L 3/00; A47K 1/04; A47F 5/00; A45B 1/02; A61H 3/04
See application file for complete search history.

(56) References Cited

U.S. PATENT DOCUMENTS

| 4,332,378 A | 6/1982 | Pryor |
| 5,110,076 A | 5/1992 | Snyder et al. |
| 6,056,249 A | 5/2000 | Fillon, Jr. |

(Continued)

FOREIGN PATENT DOCUMENTS

CN    203017494 U  *  6/2013

OTHER PUBLICATIONS

International Search Report received for PCT Patent Application No. PCT/US2016/029061, dated Aug. 8, 2016, 2 pages.

*Primary Examiner* — James A Shriver, II
*Assistant Examiner* — James J Triggs

(57) ABSTRACT

A mounting structure is disclosed for providing support to a user. The disclosed structure can operate a braking mechanism through receipt of an input from a user. The braking mechanism functions to cause the Mounting structure to resist translational movement relative to a support surface, such as the floor of a building. A vertical displacement of an input surface may alter the coefficient of friction between the support surface and the Mounting structure. Such a mounting structure can be employed to assist a user in maintaining their balance.

20 Claims, 13 Drawing Sheets

(56) References Cited

U.S. PATENT DOCUMENTS

| | | | |
|---|---|---|---|
| 7,935,030 B1* | 5/2011 | Nesbitt | A61H 3/04 |
| | | | 482/142 |
| 2003/0094191 A1 | 5/2003 | Lin | |
| 2007/0221796 A1 | 9/2007 | Silverman et al. | |
| 2011/0108075 A1* | 5/2011 | Weber | A61H 3/02 |
| | | | 135/72 |
| 2011/0198154 A1* | 8/2011 | Worley | A47C 12/00 |
| | | | 182/148 |

\* cited by examiner

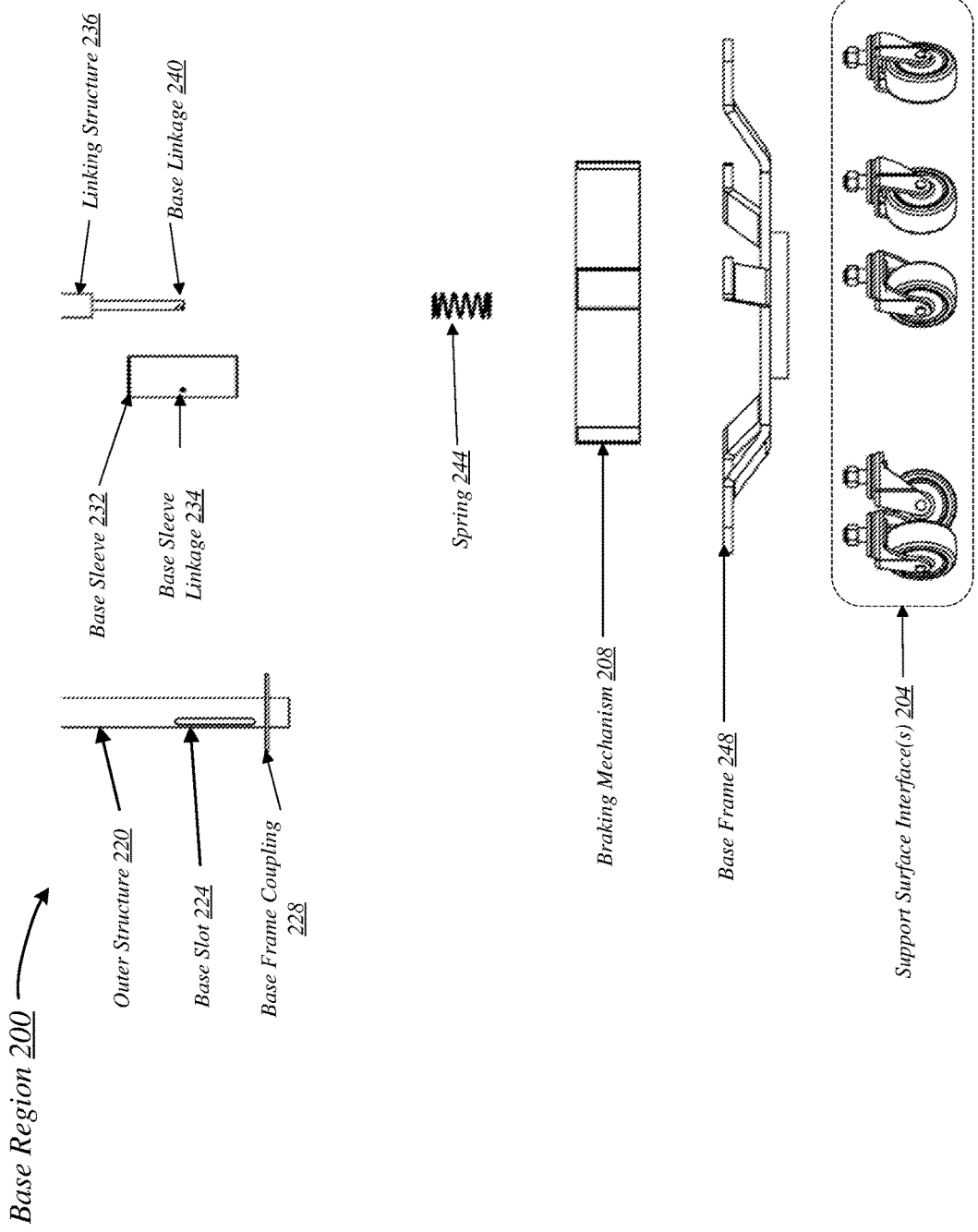

Support Surface Interface 204

Support Surface 206

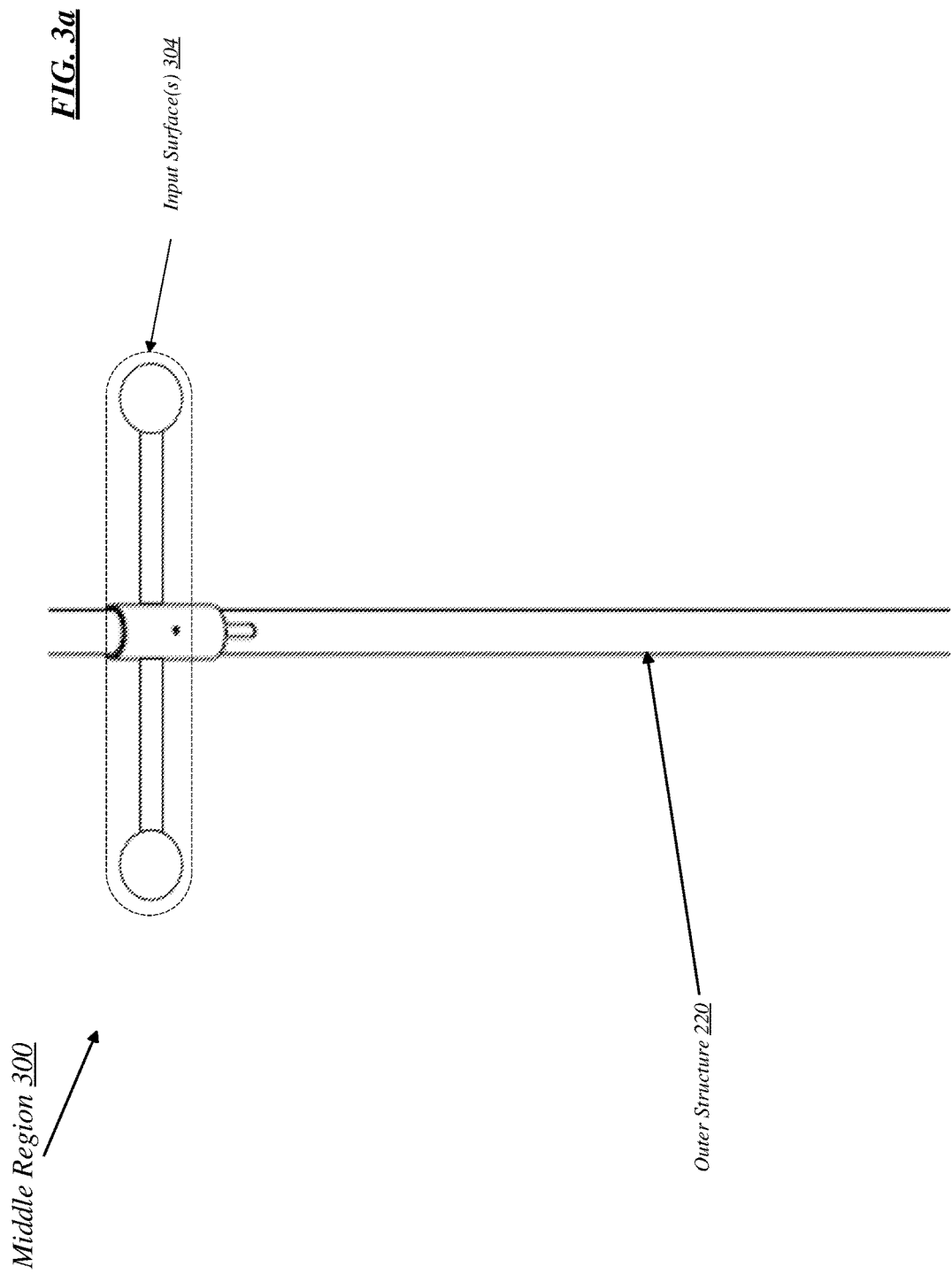

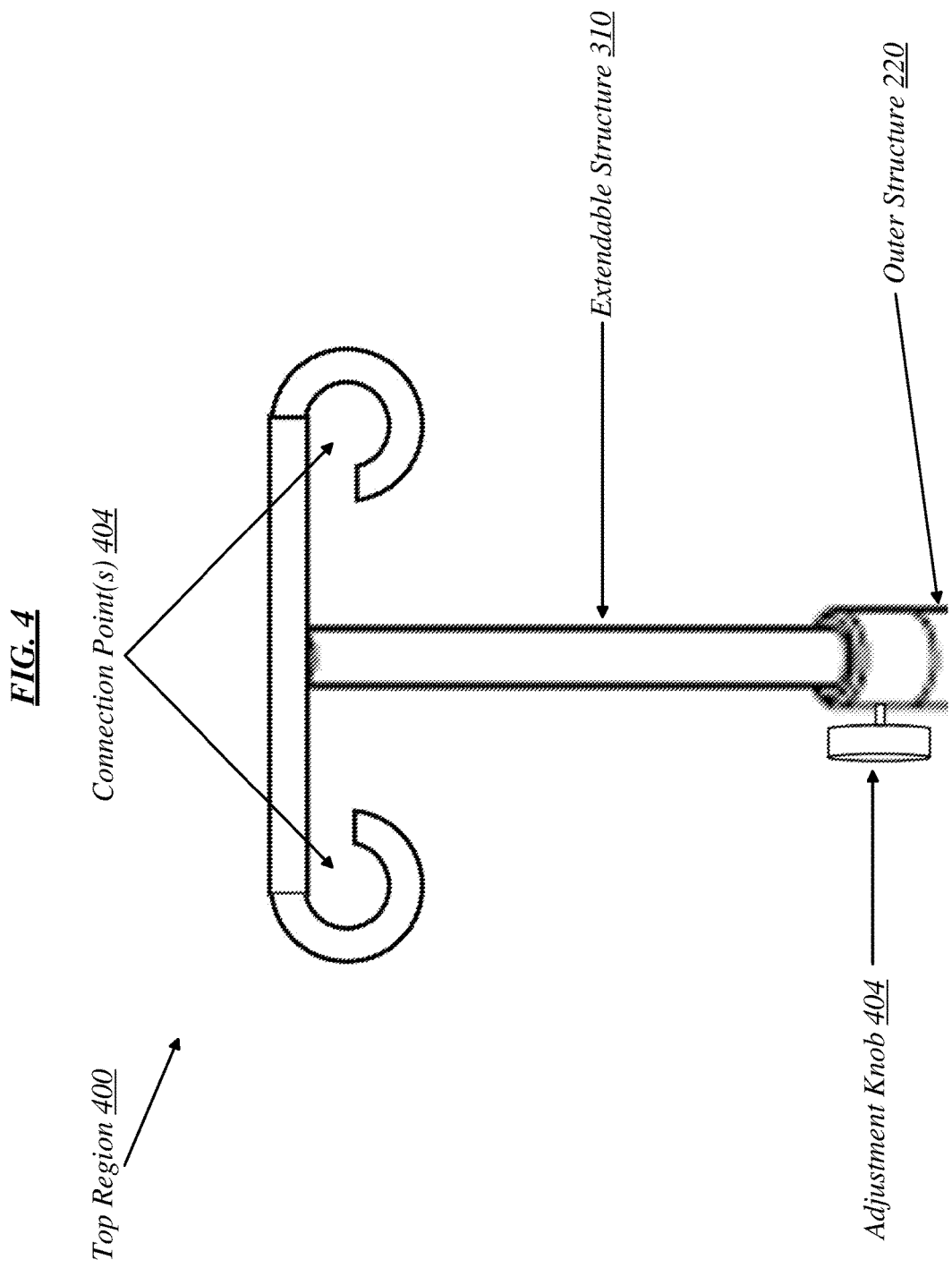

*FIG. 7*

_Storage Medium 700_

*Computer Executable Instructions for 550*

*Computer Executable Instructions for 600*

*900*

MOBILE MOUNTING STRUCTURE FOR MEDICAL EQUIPMENT

CROSS-REFERENCE TO RELATED APPLICATION

This application is a national phase application claiming the benefit of and priority to International Patent Application No. PCT/US2016/029061, entitled "Mobile Mounting Structure for Medical Equipment", filed Apr. 22, 2016, which claims the benefit of and priority to previously filed U.S. Provisional Patent Application Ser. No. 62/151,430 entitled "Mobile Mounting Structure for Medical Equipment" filed on Apr. 23, 2015, which are hereby incorporated by reference in their entireties.

BACKGROUND OF THE DISCLOSURE

Mobile mounting structures can be used to provide an attachment point for medical equipment such as intravenous (IV) fluid containers, catheter bags, infusion pumps, and devices for diagnostics, monitoring vital signs, and causing therapeutic effects in a user. In one example, the IV fluid container may hold a medication suspended in a fluid. The IV fluid container can be connected to an attachment point in a removable manner. The attachment point can be located to enable administration of the fluid to a user by converting potential energy to kinetic energy. In other current arrangements the fluid may be administered by a pump such as an infusion pump. Mobile mounting structures have also included wheels to enable them to travel with a patient enabling any attached medical equipment to remain proximate to a user.

BRIEF DESCRIPTION OF THE DRAWINGS

By way of example, exemplary embodiments of the disclosed device will now be described, with reference to the accompanying drawings, in which:

FIG. 2b is an exploded view of an exemplary embodiment of a base region in accordance with an embodiment of the present disclosure;

FIG. 3a is an exemplary embodiment of a middle region in accordance with an embodiment of the present disclosure;

FIG. 4 is an exemplary embodiment of a top region in accordance with an embodiment of the present disclosure.

FIG. 7 illustrates an embodiment of a storage medium.

DETAILED DESCRIPTION

Figure 1:
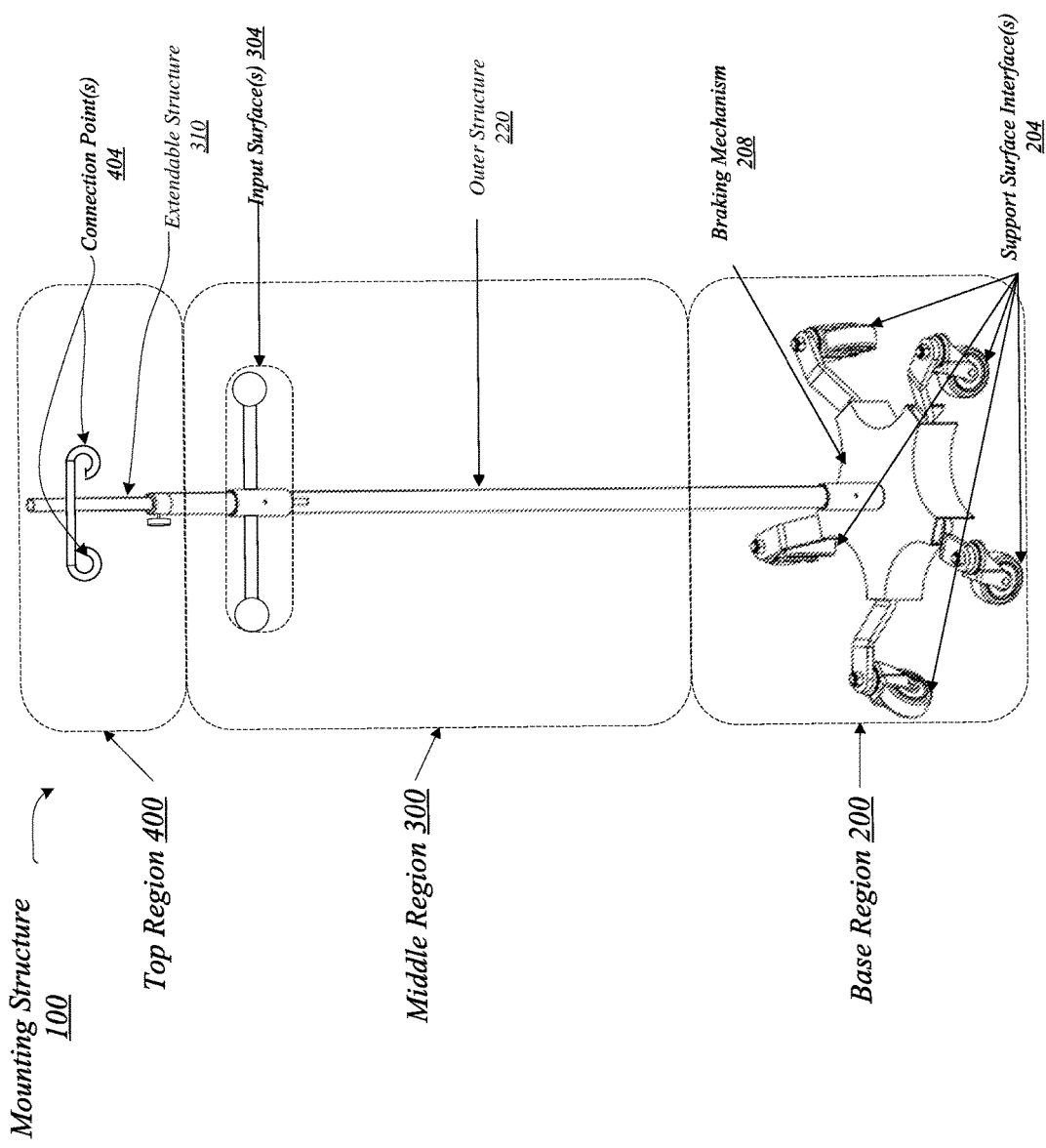
FIG. 1 is an overview of an exemplary embodiment of a mounting structure in accordance with an embodiment of the present disclosure.

Various embodiments are generally directed to mounting structures for medical equipment. Some embodiments are particularly directed to mobile mounting structures for medical equipment having dynamic braking operation. Dynamic braking operation may include one or more features to adjust the coefficient of friction between a support surface and the mounting structure to improve functionality of the mounting structure. Improving functionality of the mounting structure may include one or more of providing a stable support for a patient, positioning the mounting structure, preventing the mounting structure from tipping, and improving accessibility. For instance, a user may utilize the mounting structure as a stable support to assist with balance.

One challenge facing current arrangements is that such mobile mounting structures lack the ability to provide support to a patient or user. Current arrangements do not restrict translational motion if a user needs additional support. When a user loses their balance current arrangements do not provide a stable support. This deficiency can fail to prevent or cause an injury. Adding further complexity, a user may need additional devices to act as a stable support. These additional devices can increase the burden on a user, making safe ambulation difficult or impossible. For instance, using a walker with an infusion pump stand may prevent a patient from ambulating in a safe manner without excessive assistance.

In view of the foregoing, the present disclosure provides several technical effects and advantages relative to conventional mounting structure technologies and solutions. In various embodiments, these technical effects may include increasing the functionality of mounting structures for medical equipment and/or improving patient safety. For example, a mounting structure for medical equipment may be provided that can restrict a translational motion of the mounting structure in a manner to reduce the potential of a patient being injured. In some embodiments, a mounting structure may enable a user to steady their balance. In various embodiments, the mounting structure may utilize an intuitive interface surface to allow a user to restrict the translational motion of the mounting structure.

An exemplary embodiment of a mounting structure in accordance with the present disclosure can include a mounting structure with a top region, a middle region, and a base region. The middle region can be interposed between the top region and the base region. The base region can include a support surface interface and a braking mechanism. The support surface interface may facilitate movement of the mounting structure relative to a support surface. The braking mechanism may be configured to cause the mounting structure to resist movement relative to the support surface. The top region can include a connection point. The connection point may be configured to couple with a container comprising a fluid that may be administered to a user. The middle region can include an input surface. The input surface may receive an input from the user. The received input can activate the braking mechanism, wherein activation of the braking mechanism causes the mounting structure to resist movement relative to the support surface in a plurality of dimensions.

Another exemplary embodiment of a mounting structure in accordance with the present disclosure can include a base configured to move a mounting structure relative to a support surface. A braking mechanism can operate to cause the mounting structure to resist the movement relative to a support surface. An activation interface can receive input and the input may cause the braking mechanism to activate, thereby causing the mounting structure to resist the movement relative to the support surface. A distance of the activation interface relative to the support surface may be selectively adjustable.

An exemplary method for providing support, including: receiving input at an input surface, the input surface configured to operate a braking mechanism; and altering the coefficient of friction between an mounting structure and a support surface in response to operation of the braking mechanism.

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present embodiments will now be described more fully hereinafter with reference to the accompanying drawings, in which some embodiments are shown. The subject matter of the present disclosure, however, may be embodied in many different forms and should not be construed as limited to the embodiments set forth herein. Rather, these embodiments are provided so that this disclosure will be thorough and complete, and will fully convey the scope of the subject matter to those skilled in the art. One of ordinary skill in the art will understand that the systems, devices, and methods disclosed may easily be reordered and manipulated into many configurations, provided they are not mutually exclusive.

In general, a mounting structure is disclosed for providing support to a user. The disclosed system can include an input surface for receiving input from a user to operate a braking mechanism. The braking mechanism may cause the mounting structure to resist movement relative to a support surface, such as the floor of a building. Such a mounting structure can be employed to assist a user in maintaining their balance. In some embodiments, a vertical displacement of the input surface can alter the coefficient of friction between the support surface and the mounting structure.

Referring now to FIG. 1, a mounting structure 100 consistent with a non-limiting, exemplary embodiment of the present disclosure is shown. The mounting structure 100 can include a base region 200, a middle region 300, and a top region 400. Embodiments are not limited in this context.

The base region 200 can include a braking mechanism 208 and one or more support surface interface(s) 204. The support surface interface(s) 204 can facilitate movement of the mounting structure 100 relative to a support surface 206 (see FIG. 2c). The braking mechanism 208 may cause the mounting structure 100 to resist a movement relative to the support surface 206.

The middle region 300 can include one or more input surface(s) 304. The input surface(s) 304 may activate the braking mechanism 208 upon receiving appropriate user input. The input surface(s) 304 may provide a handle or a place for a user to grip and maneuver the mounting structure 100. In some embodiments, the input surfaces 304 can activate the braking mechanism 208 through application of sufficient force. The amount of force required to activate the brake may be adjustable and customizable for individual user needs. For example, the required force to activate the braking mechanism 208 may be less for a lighter weight user relative to a heavier user. The amount of force required to activate the brake may be configured such that the braking mechanism 208 is intuitive to use while minimizing unintentional or accidental activation of the brake. It will be appreciated that while the illustrated embodiment of the input surface(s) 304 can activate the braking mechanism 208 in response to a downward displacement, other displacements and arrangements can additionally or alternatively be implemented. For example, a lateral, upward, and/or downward for may be required to activate the braking mechanism 208.

The top region 400 can include one or more connection point(s) 404. The connection point(s) 404 may enable medical equipment to attach to the mounting structure 100. The medical equipment can include one or more of an intravenous (IV) fluid container, catheter bag, infusion pump, and/or device for diagnostics, monitoring vital signs, and/or causing therapeutic effects in a user. For example, a container comprising a fluid for administration to a user body may attach to the mounting structure 100 by a connection point 404. As will be appreciated, the mounting structure 100 can employ a variety of arrangements to provide support to a user. Such arrangements will be discussed in greater detail below.

In certain embodiments, the base, middle, and top regions 100, 200, 300 can contain one or more of the same components or portions thereof. Portions of the outer structure 220 may be included in the top, middle, and bottom regions as the outer structure 220 may extend up from the bottom region 200 into and through the middle region 300, terminating in the top region 400. Additionally, different components may be located in a first region when the mounting structure 100 is in a first state and located in a second region when the mounting structure 100 is in a second state.

For example, medical equipment may be located in one or more of the bottom region 200, middle region 300, and/or top region 400. In one non-limiting exemplary embodiment, the outer structure 220 may include one or more connection points 404 for attaching medical equipment comprising one or more of an intravenous (IV) fluid container, catheter bag, infusion pump, and/or device for diagnostics, monitoring vital signs, and/or causing therapeutic effects in a user. In some embodiments, one or more types of medical equipment can readily be attached to an outer structure 220 with no requirement of a connection point.

The connection points 404 may be configured such that the orientation of an attached medical equipment, relative to the support surface 206, can be altered. Altering the orientation of the attached medical equipment can make monitoring and operating the medical equipment easier. For example, an infusion pump attached to the mounting structure 100 may be configured such that a display of the infusion pump has an upward orientation away from the support surface 206.

In various embodiments, the mounting structure 100 may include one or more electronic components including a battery, memory, outlet, surge protector, processor, sensor, signal processing circuitry, motor, and/or actuator. In some embodiments, an electrical component of the mounting structure 100 can be part of and/or communicatively coupled to a computer or computer system. The electronic components may assist in one or more capacities in providing support to a user and will be described in more detail below.

One of ordinary skill in the art will appreciate that the base, middle, and top regions can readily be combined or arranged in any manner relative to each other as long as the mounting structure 100 is able to provide support to a user. Furthermore, it will be appreciated by one having ordinary skill in the art that the mounting structure arrangements described in FIG. 1 can be readily combined or modified. For example, the base region may include a battery for providing power to one or more electrical components in the mounting structure 100; by locating the battery in the base region the center of gravity of the mounting structure 100 can be lowered. In some embodiments, mounting structure 100 may include a holder for a tank of compressed gas (e.g., oxygen tank). In some embodiments, the holder may include tube management features to prevent tubes from tangling.

Figure 2A:
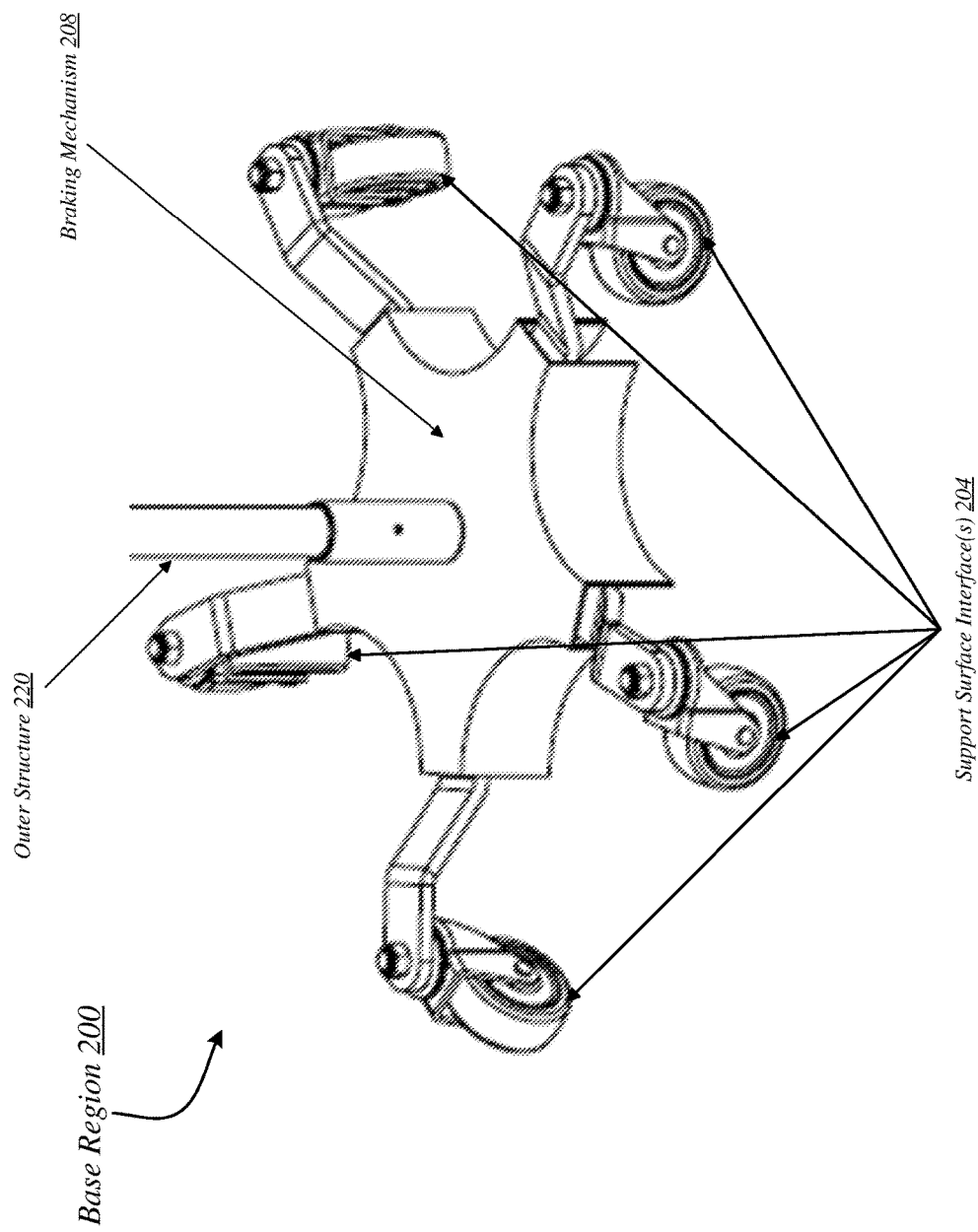
FIG. 2a is an exemplary embodiment of a base region in accordance with an embodiment of the present disclosure.

FIG. 2a is a base region 200 consistent with a non-limiting, exemplary embodiment of the present disclosure. (It will be appreciated that the base region 200 of FIG. 1 may include any or all of the features of the base region 200 of FIG. 2a.) The base region 200 may include a portion of the outer structure 220, linking structure 236, and/or the extendable structure 310. In the non-limiting exemplary illustrated embodiment, the base region 200 can include a braking mechanism 208 and one or more support surface interface(s) 204. The support surface interface(s) 204 can facilitate movement of the mounting structure 100 relative to a support surface 206 (see FIG. 2c). The braking mechanism 208 may cause the mounting structure 100 to resist a movement relative to the support surface 206. Embodiments are not limited in this context.

In the illustrated embodiment, the braking mechanism 208 and the support surface interface 204 operate independently. The support surface interface 204 may enable the mounting structure 100 to move relative to a support surface 206 (see FIG. 2c). The braking mechanism 208 may cause the mounting structure 100 to resist movement by coming into contact with the support surface 206.

In some embodiments, the ability of the braking mechanism 208 to cause the mounting structure 100 to resist movement is dependent on the support surface interface 204. For example, the support surface interface 204 may comprise a plurality of wheels wherein at least one of the wheels is arranged such that activation of the braking mechanism restricts the wheels ability to rotate, thereby causing the mounting structure 100 to resist movement relative to a support surface 206 (see FIG. 2c). In some embodiments, a secondary braking mechanism (not shown) can be located in the base region 200 and may be used to lock the mounting structure 100 and prevent the mounting structure 100 from moving, relative to the support surface when the braking mechanism 208 is not activated.

In some embodiments, the base region 200 may include a cord and/or tube management system (not shown). The cord and/or tube management system may provide routing, reduced clutter, and easy cord and/or tube tracing. The cord and/or tube management system may include one or more of a clip, spiral structure, "c", "s", or similar structure, cavities, and/or channels.

In some embodiments, the base region 200 may include one or more electronic components such as a battery, a memory, a processor, a sensor, and an actuator. For example, the base region 200 may comprise a self-balancing robotic device. The self-balancing robotic device may be constructed with one or more gyroscopes. Upon detecting movement of the mounting structure, the self-balancing robotic device may make the appropriate movements to maintain the mounting structure in an inverted pendulum configuration, wherein the top region comprises the inverted pendulum.

In one non-limiting exemplary embodiment, the braking mechanism 208 may be activated/deactivated by an electronic actuator. In some embodiments, one or more electronic components may provide assistance for maneuvering the mounting structure 100. For example, one or more electronic motors may be configured to move the mounting structure 100 in a desired direction. One of ordinary skill in the art will appreciate that one or more electronic components could be arranged to provide or assist in any functional aspect of the mounting structure 100. In some embodiments, haptic feedback may be used to alert a user of the state of one or more electronic components such as sensors and motors.

It will be appreciated by one having ordinary skill in the art that the base region 200 arrangements described in FIG. 2a can be readily combined or modified. For example, the support surface interface 204 may include a spherical drive system.

FIG. 2b is an exploded view of a base region 200 consistent with a non-limiting, exemplary embodiment of the present disclosure. It will be appreciated that the base region 200 of FIG. 1 may include any or all of the features of the base region 200 of FIG. 2b. In the illustrated embodiment, the base region 200 includes support surface interfaces 204, comprising five caster wheels. The caster wheels may be able to move in any direction in plane with a support surface 206 (see FIG. 2c) and rotate 360 degrees. Each caster wheel can include threaded studs for attaching the caster wheels to a base frame 248. Embodiments are not limited in this context.

In some embodiments, the base frame 248 may include a plurality of legs extending from a central body. However, the base frame can include any arrangement connecting the outer structure 220 to the support surface interface(s) 204. In the illustrated embodiment, the base frame 248 may be arranged in a spider leg configuration with a plurality of legs. The spider leg configuration can lower the center of gravity of the mounting structure 100 by reducing the vertical distance from the support surface 206 (see FIG. 2c) and the base frame 248, thereby reducing the tipping hazards and increasing the stability of the mounting structure 100.

A through hole may be located proximate to the end of each spider leg. The caster wheels can be attached to a base frame 248 by inserting the threaded stud of each caster wheel into the through hole located proximate to the end of respective spider legs, wherein the threaded studs partially extend above an upper surface of the base frame 248. The caster wheels may then be coupled to the base frame 248 by securing a nut on the end of the portion of the threaded stud of each caster wheel penetrating the through hole located proximate to the end of respective spider legs.

The base frame 248 can also include a central receptacle disposed in the upper surface with one or more threaded receptacles surrounding the central receptacle. A spring 244 can then be seated in the central receptacle. A base end of the outer structure 220 may be inserted into the central receptacle such that it surrounds the spring 244. When the base end of the outer structure 220 is fully inserted into the central receptacle, a base frame coupling 228 may contact the upper surface of the base frame 248.

The base frame coupling 228 can also include one or more through holes. The one or more through holes may correspond to each of the one or more threaded receptacles surrounding the central receptacle of the base frame 248. The base end of the outer structure 220 can be coupled to the base frame 248 by inserting a bolt, pin, or comparable structure through each of the one or more through holes in the base frame coupling 228 and threading the bolt, pin, or comparable structure into the one or more corresponding threaded receptacles surrounding the central receptacle of the base frame 248.

Figure 2C:
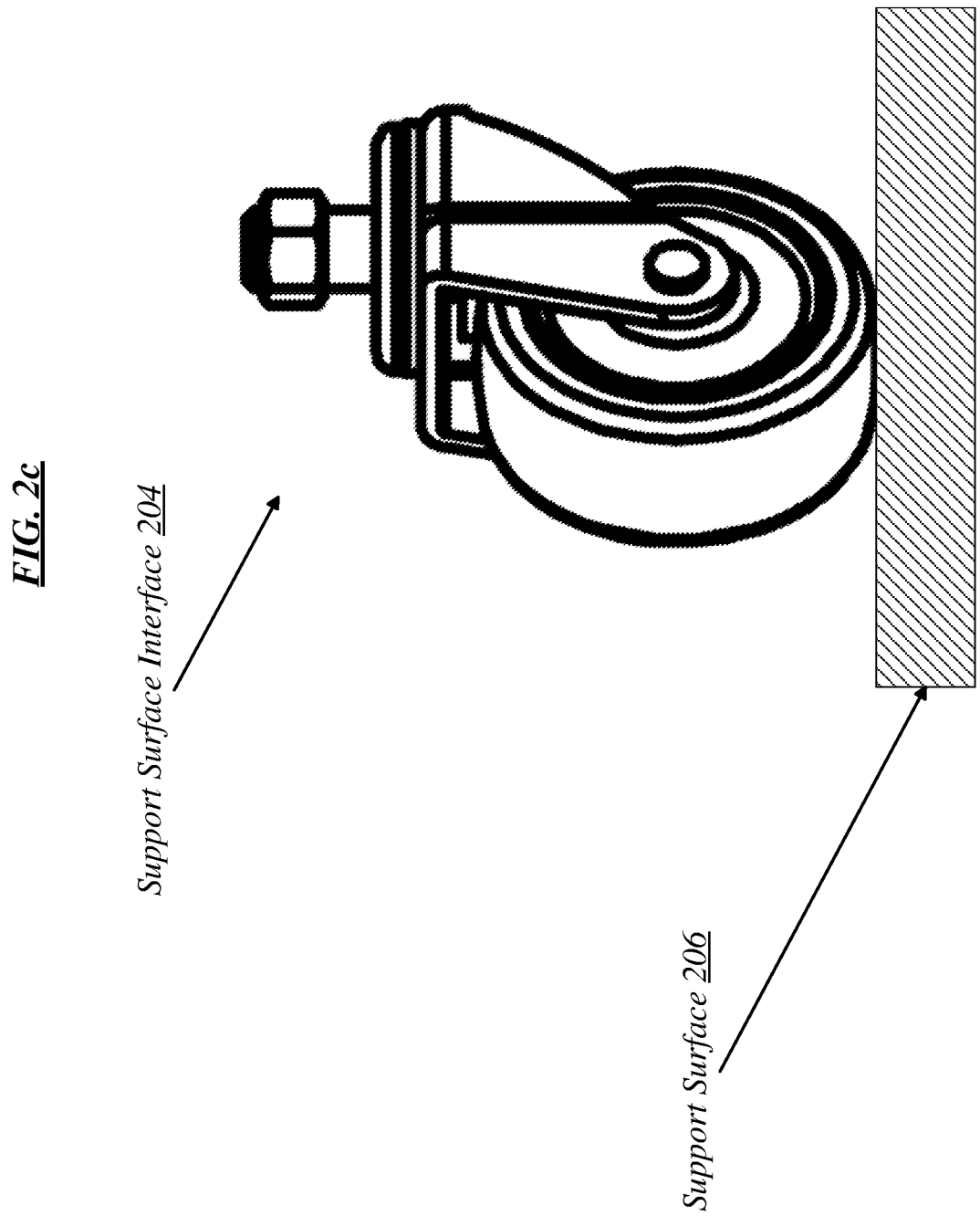
FIG. 2c is an exemplary embodiment of support surface interface(s) in accordance with an embodiment of the present disclosure.
Figure 2D:
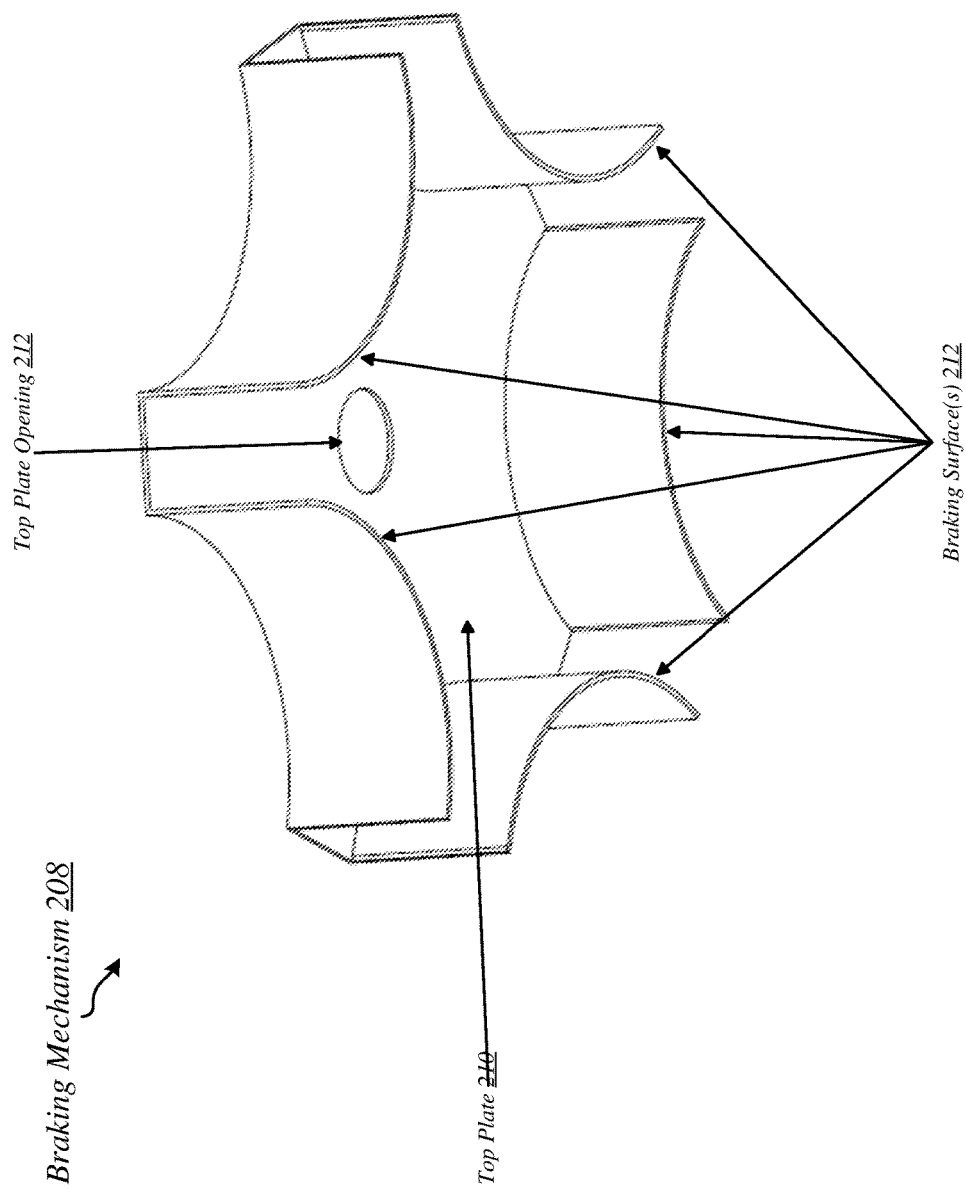
FIG. 2d is an exemplary embodiment of a braking mechanism in accordance with an embodiment of the present disclosure.

The braking mechanism 208 may be disposed on top of the base frame 248 with the outer structure 220 extending though a top plate opening 212 (see FIG. 2*d*). The base sleeve 232 can be disposed on top of the braking mechanism 208 with the outer structure extending through the base sleeve 232. The braking mechanism 208 and the base sleeve 232 may be coupled together via a weld.

In the illustrated embodiment, a linking structure 236 can mechanically link the input surface 304 and the braking mechanism 208. The linking structure 236 can be inserted, at least in part, in the interior of the outer structure 220. The linking structure 236 may rest on top of the spring 244. The base sleeve 232, outer structure 220, and the linking structure 235 may then be aligned such that a bolt, pin, or comparable structure can extend through a base sleeve linkage 234 of the base sleeve 232, through a base slot 224 of the outer structure 220, and through the base linkage 240 of the linking structure 236 thereby securing the base sleeve 232 to the linking structure 236. The base sleeve 232 and the linking structure 236 may then displace vertically the length of the base slot 224.

The spring 244 may exert a sufficient force on the linking structure 236 such that the bolt, pin, or comparable structure connecting the outer structure 220 and the linking structure 236 can press against the top of the base slot 224 when the mounting structure 100 is in a non-braked steady state. In the illustrated embodiment, the braking mechanism 208 may be activated when a user applies a force to input surface(s) 304 sufficient to compresses the spring 244 and cause the braking mechanism 208 to contact the support surface 206 (see FIG. 2*c*). Some embodiments may include a plurality of braking mechanisms 208. Further, various embodiments may include a linking structure with one or more mechanical linkages including cables, pulleys, levers, and/or gears.

It will be appreciated that while the illustrated embodiment of the linking structure 236 employs a mechanical linkage, other linking structures and arrangements can additionally or alternatively be implemented. For example, the linking structure may include one or more wireless transponders configured to communicatively couple. The wireless transponders may utilize a defined interface. In some embodiments, the defined interface may include one or more wireless communication protocols, such as one or more Institute of Electrical and Electronics Engineers (IEEE) standards, for example.

In some embodiments the distance of displacement of the input surface(s) 304 for engaging the braking mechanism 208 can be adjusted. For example, in the illustrated embodiment, the base linkage 240 may be a partially threaded. Rotating the base linkage 240 can alter the overall length of the linking structure 236. Altering the overall length of the linking structure 236 can adjust the distance the input surface(s) 304 needs to displace to activate the braking mechanism 208.

In some embodiments an effective spring constant of the spring 244 may be adjustable. In certain embodiments, an adjustable spacer (not shown) may be inserted between the spring and the floor of the central receptacle of the base frame 248. Adjusting the spacer can alter the effective spring constant by adjusting a compression of the spring 244, thereby making the amount of force required to activate the brake adjustable and customizable for individual user needs. For example, a male user may desire to apply more force to activate the breaking mechanism than a female user, thereby reducing the probability of accidental activation of the braking mechanism. The male user can increase the effective spring constant by increasing the non-braked steady state compression of the spring 244.

In some embodiments, the braking mechanism 208 may be integrated into the base frame 248. For example, legs extending from a central body may be able to bend about a pivot point, upon a determinable amount of force, resulting in a squatting action of the mounting structure. The squatting action may be able to cause a portion of the mounting structure to contact the support surface, thereby restricting the ability of the mounting structure to move relative to the support surface.

It will be appreciated by one having ordinary skill in the art that the base region described in FIG. 2*b* can be readily combined or modified. For example, the linking structure 236 can include a brake cable that may mechanically link the input surface 304 to the braking mechanism 208.

Referring now to FIG. 2*c*, a support surface interface 204 and a support surface 206 consistent with a non-limiting, exemplary embodiment of the present disclosure is shown. It will be appreciated that the support surface interface 204 of FIG. 1 may include any or all of the features of the support surface interface(s) 204 of FIG. 2*c*. The mounting structure 100 can include one or more support surface interface(s) 204. The support surface interface(s) 204 may comprise any arrangement capable of supporting the weight of the mounting structure 100 and facilitating movement of the mounting structure 100 relative to the support surface 206. In some embodiments the support surface interface may be configured to traverse cords and/or tubes without sticking or becoming stuck. Embodiments are not limited in this context.

The support surface 206 can be any generally planar surface large enough to carry the weight of at least one support surface interface 204 of the mounting structure 100. In some embodiments the support surface 206 is the floor of a building such as a hospital, healthcare facility, or personal residence. A plurality of adjacent support surfaces 206 may support one or more of the support surface interfaces 204.

It will be appreciated that while the illustrated embodiment of the support surface interface(s) 204 comprise five caster wheels, other support surface interface(s) 204 can additionally or alternatively be implemented. The support surface interface(s) 204 may comprise any arrangement capable of supporting the weight of the mounting structure 100 and facilitating movement of the mounting structure 100. For example, the support surface interface(s) 204 may comprise arrangements including devices such as tracks, legs, wheels, spheres, or anything comparable.

It will be appreciated by one having ordinary skill in the art that the support surface interface arrangements described in FIG. 2*c* can be readily combined or modified. For example, the support surface interface(s) can include a magnetic material and a corresponding electro-magnet may be located in the floor. When the electro-magnet is energized, it may lock the mounting structure 100 in place and may prevent mounting structure 100 from tipping over and/or sliding. In some embodiments, a magnetic material may be included in the base frame 248.

FIG. 2*d* is a braking mechanism 208 consistent with a non-limiting, exemplary embodiment of the present disclosure. It will be appreciated that the braking mechanism 208 of FIG. 1 may include any or all of the features of the support surface interface(s) 204 of FIG. 2*d*. The braking mechanism 208 may include a top plate 210. The top plate 210 can include a top plate opening 212. One or more of the outer structure 220, base sleeve 232, linking structure 236, spring 244, or extendable structure 310 (see FIG. 3b) may extend through the top plate opening 212. Embodiments are not limited in this context.

In some embodiments, the braking mechanism 208 and the support surface interface 204 may operate independently. For example, in the illustrated embodiment, the braking mechanism 208 can include braking surface(s) 212. Activation of the braking mechanism 208 may cause braking surface(s) 212 to contact the support surface 206. The friction between the support surface 206 and the braking surface(s) 212 can act to resist movement of the mounting structure 100 relative to the support surface 206. In certain embodiments, activation of the braking mechanism 208 may cause the top plate 210 to contact the top of the base frame 248.

In other embodiments, the ability of the braking mechanism 208 to cause the mounting structure 100 to resist movement can be dependent on the support surface interface(s) 204. In some embodiments, the braking mechanism 208 may include a wheel brake. For example, the support surface interface(s) 204 may comprise a plurality of wheels wherein at least one of the wheels is arranged such that activation of the braking mechanism 208 can restrict the ability to rotate of at least one wheel, thereby causing the mounting structure 100 to resist movement relative to a support surface 206. The braking mechanism may restrict the ability of support surface interface 204 to move relative to the support surface 206 through any practical arrangement such as frictional brakes, pumping brakes, or electromagnetic brakes.

The braking mechanism 208 may generally employ a non-braked and/or braked steady state. A non-braked steady state can mean that the braking mechanism 208, when the mounting structure 100 is unlocked and not receiving user input, is not activated. In other words, in an non-braked steady state a user may move the mounting structure 100 relative to a support surface 206 (see FIG. 2c) without using the input surface. For example, the mounting structure 100 may readily move with a user and the braking mechanism 208 may require continuous user input to remain activated.

In some embodiments, a braked steady state may be utilized. A braked steady state can mean that the braking mechanism 208, when the mounting structure 100 is unlocked and not receiving user input, is activated. In other words, in a braked steady state a user may have to use the input surface(s) 304 to deactivate the braking mechanism prior to moving the mounting structure 100 relative to a support surface 206 (see FIG. 2c).

The illustrated embodiment of the exemplary mounting structure 100 utilizes the non-braked steady state, however, one of ordinary skill in the art will appreciate that the features and embodiments described herein can readily be incorporated into a mounting structure utilizing either a braked or non-braked steady state. For example, a mounting structure 100 employing a braked steady state may receive a first user input to lock the braking mechanism 208 in an deactivated configuration and a second user input may unlock the braking mechanism 208, thereby activating the braking mechanism.

In some embodiments, the braking surface 212 is covered or coated in a material such as rubber, or a polymer coating. However, the coating or covering material may be any material that develops a desired coefficient of friction with the support surface 206. The desired coefficient of friction between the support surface 206 and the braking surface(s) 212 may enable the mounting structure 100 to stop movement relative to the support surface 206 until a lateral force applied to the mounting structure 100 approaches a force sufficient to cause the mounting structure 100 to tip over. When a lateral force sufficient to cause the mounting structure 100 to tip over is applied, the mounting structure 100 may begin to slide on the support surface 206 while the braking surface(s) 212 are in contact with the support surface. In some embodiments, the braking mechanism 208 can include a flange to increase the surface area contacting the support surface 206.

It will be appreciated by one having ordinary skill in the art that the interface surface arrangements described in FIG. 2d can be readily combined or modified. For example, the braking mechanism 208 may extend through the base frame 248 to contact the support surface 206.

Referring now to FIG. 3a, a middle region 300 consistent with a non-limiting, exemplary embodiment of the present disclosure is shown. It will be appreciated that the middle region 300 of FIG. 1 may include any or all of the features of the middle region of FIG. 3a. The middle region 300 can include one or more input surface(s) 304. The input surface(s) 304 may activate the braking mechanism 208 upon receiving appropriate user input. Embodiments are not limited in this context.

In the illustrated embodiment, the input surface(s) 304 can include a handle or a place for a user to grip and/or maneuver the mounting structure 100. The input surfaces 304 can activate the braking mechanism through application of sufficient force to and/or displacement of the input surface(s) 304. In other embodiments, regarding a braked steady state, as described above, the braking mechanism can be deactivated by sufficient force applied to and/or displacement of the input surface(s) 304. In some embodiments, the braking mechanism can be activated/deactivated by sufficient force applied to and/or displacement of less than all of the input surfaces 304. Activation of the braking mechanism 208 via the input surface(s) 304 may be configured such that the braking mechanism 208 is intuitive to use while minimizing unintentional or accidental activation of the brake.

In some embodiments, utilizing a non-braked steady state, activation of the braking mechanism 208 via the input surface(s) 304 can lock the braking mechanism 208 in the activated state and a second application of sufficient force to and/or displacement of the input surface(s) 304 may be required to unlock and deactivate the braking mechanism. In other embodiments, utilizing a braked steady state, deactivation of the braking mechanism 208 via the input surface(s) 304 can lock the braking mechanism 208 in the deactivated state and a second application of sufficient force to and/or displacement of the input surface(s) 304 may be required to unlock and deactivate the braking mechanism 208. This arrangement can allow a user to easily lock and unlock the braking mechanism 208.

As will be appreciated, the input surface(s) 304 can employ a variety of arrangements to enable a user to activate the braking mechanism 208. Some embodiments include a plurality of input surfaces 304, while other embodiments include a single input surface 304. For example, a plurality of input surfaces 304 may include two or more levers or a single input surface 304 may include a toroidal shape. In some embodiments, the input surface 304 can include a handle receiver and/or a handle. One of ordinary skill will appreciate that any configuration with an appropriate size and strength can be used for the input surface(s) 304.

In some embodiments, the height of the input surface 304 relative to the support surface 206 may be adjustable. The user may adjust the height of the input surface 304 to their personal preference. For example, a user that is short in stature may adjust the input surface 304 so that it is closer to the support surface 206 and a user that is tall in stature may adjust the input surface 304 so that it is further from the support surface 206.

In some embodiments, the input surface may be arranged asymmetrically. In one non-limiting example, the input surface may only be located on one side of the mounting structure; this arrangement may be used to encourage a user to use the mounting structure 100 only from desirable positions or orientations relative to the mounting structure 100. An asymmetric input surface can discourage users from rotating the mounting structure 100 and may prevent tube or cords on or about the mounting structure 100 from becoming entangled or wrapped. In some embodiments, a cord and/or tube management system may be placed on the opposite side of the mounting structure relative to an asymmetric input surface.

The input surface 304, linking structure 236, braking mechanism 208, or any other component of the mounting structure 100 may include one or more electrical components to realize functional aspects of the mounting structure 100 such as communication through wired or wireless connections. In some embodiments, the one or more electrical components may include one or more electronic components such as a battery, a memory, a processor, a sensor, and an actuator. For example, the input surface 304 can include an electronic switch configured to activate the braking mechanism 208. In some embodiments, the input surface(s) 304 may be removable or separate from the mounting structure 100. For example, the input surface may be attached to the mounting structure by a cord, such as a retractable cord.

In some embodiments the input surface communicates with and/or activates the braking mechanism 208. In other embodiments, the input surface 304 may communicate with the linking structure 236 and the linking structure 236 may activate the braking mechanism 208. In one instance, the input surface 304 includes a separate module. For example, an input surface may be a pendant with a button; when the button is pressed, the input surface wirelessly communicates with a linking structure, the linking structure may then activate the braking mechanism through a wired communication channel.

In some embodiments the input surface(s) 304 may glow in the dark or include one or more features to enable a user to locate the input surface(s) 304 such as lights disposed on the input surface(s) 304. In one non-limiting example, the mounting structure may detect movement relative to a support surface and in response facilitate one or more of the following turn on a light, activate an alarm, produce an audible noise, or transmit a wireless control signal.

In some embodiments, the mounting structure 100 can communicate with one or more accelerometers, the accelerometers may automatically cause the braking mechanism to activate upon detecting acceleration above a predetermined amount. The accelerometer may be attached to the mounting structure 100 or to a user. The mounting structure 100 may also be able to detect its speed relative to the support surface and cause the braking mechanism to activate when a predetermined speed is exceeded.

In some embodiments, the middle region may include a cord and/or tube management system (not shown). The cord and/or tube management system may provide routing, reduced clutter, and easy cord and/or tube tracing. The cord and/or tube management system may include one or more of a clip, spiral structure, "c", "s", or similar structure, cavities, and/or channels.

It will be appreciated by one having ordinary skill in the art that the interface surface arrangements described in FIG. 3a can be readily combined or modified. For example, input surface 304 may be disposed on the top end of the outer structure and the input surface 304 may be a push button or switch.

Figure 3B:
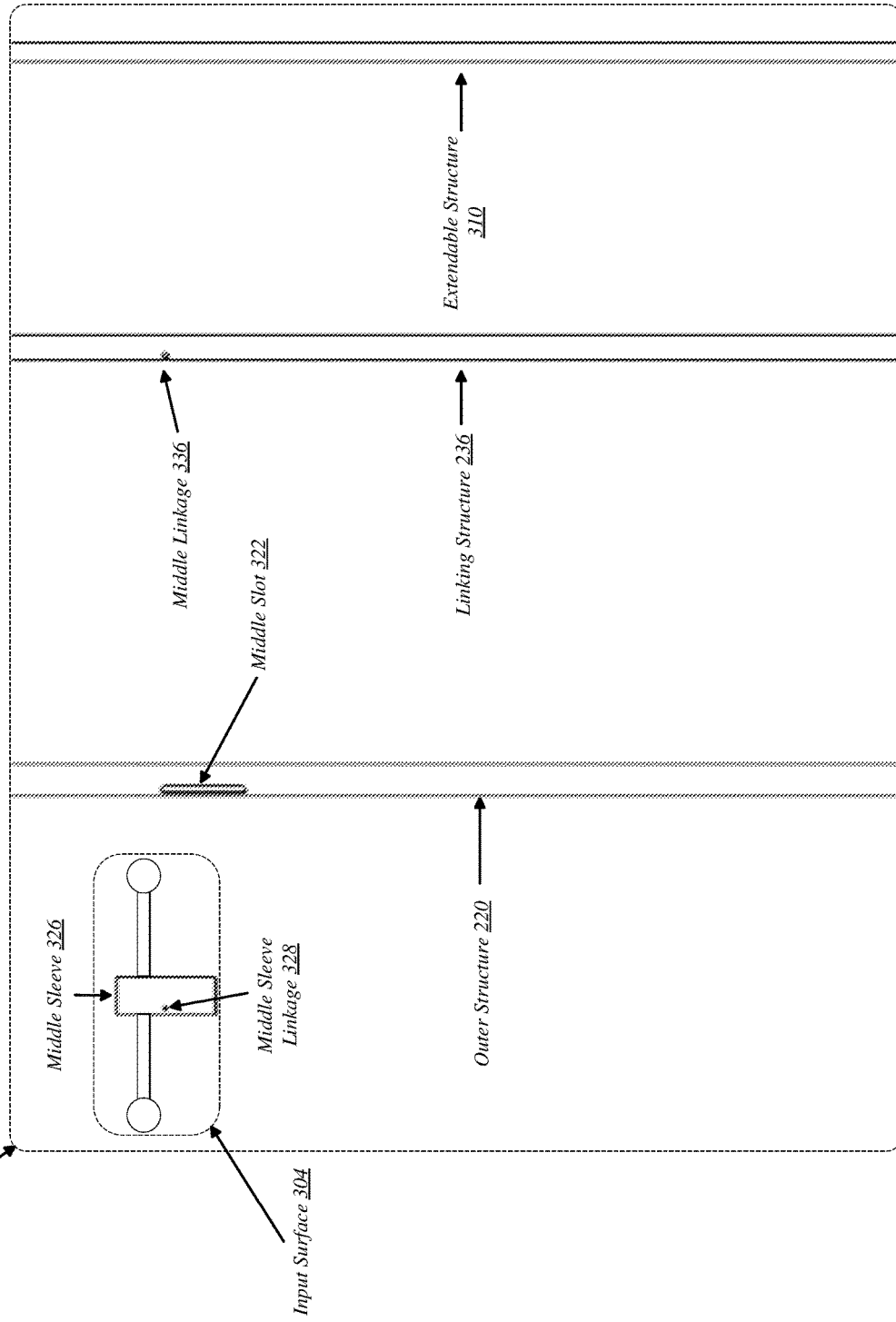
FIG. 3b is an exploded view of an exemplary embodiment of a middle region in accordance with an embodiment of the present disclosure.

FIG. 3b is an exploded view of a middle region 300 consistent with a non-limiting, exemplary embodiment of the present disclosure. It will be appreciated that the middle region 300 of FIG. 1 may include any or all of the features of the middle region of FIG. 3b. In the illustrated embodiment, the middle region 200 can include an input surface 304 and the input surface 304 can include a middle sleeve 326 and a middle sleeve linkage 328. In some embodiments the input surface 304 may include a handle. The middle region 200 may include portions of the outer structure 220, linking structure 236, and extendable structure 310. Embodiments are not limited in this context.

In some embodiments, the outer structure 220, linking structure 236, and/or extendable structure 310 may extend through the middle sleeve 326. In the illustrated embodiment, a portion of the extendable structure 310 can be disposed within the linking structure 236 with a portion of the linking structure 236 disposed within the outer structure 220, and the outer structure 220 may extend through the middle sleeve 326. The middle linkage 336 can include a threaded opening.

Inserting a bolt, pin, or comparable structure that may be threaded through the middle sleeve linkage 328, through the middle slot 322, and threading the bolt, pin, or comparable structure that may be threaded into the middle linkage 336 can connect the middle sleeve 326 and the linking structure 236. This arrangement can link the input surface 304 and the braking mechanism 208. For example, the braking mechanism 208 can be coupled to the base sleeve linkage 234, which may connect to the linking structure 236 through the base linkage 240, and the linking structure 236 can connect to the input surface 304 through the middle sleeve linkage 328.

The middle sleeve 326 and the linking structure 236 may move up and down together to the extents of the middle slot 322. In one non-limiting example, the middle sleeve and the linking structure may be biased to the top of the middle slot by the spring seated in the central receptacle of the base frame; moving the middle sleeve and the linking structure down, by applying a force to the input surface, may compress the spring activating the braking mechanism.

In some embodiments at least a portion of the extendable structure 310 can be disposed within the linking structure 236 with at least a portion of the linking structure 236 disposed within the outer structure 220 and the outer structure 220 may extend through the middle sleeve 326. A bolt, pin, or comparable structure may be inserted through the middle sleeve linkage 328, through the middle slot 322, through the middle linkage 336, through an extendable structure slot (not shown), and back out through corresponding features on the opposite side of the extendable structure slot (not shown), linking structure 236, outer structure 220, and middle sleeve 326. In some embodiments a nut, pin, or comparable locking mechanism can be used to secure the bolt, pin, or comparable structure and prevent it from backing out.

It will be appreciated by one having ordinary skill in the art that the middle region arrangements described in FIG. 3b and can be readily combined or modified. For example, the input surface may activate the braking mechanism through a wired connection with an electronic actuator disposed on the braking mechanism.

FIG. 4 is a top region 400 consistent with a non-limiting, exemplary embodiment of the present disclosure. It will be appreciated that the top region 400 of FIG. 1 may include any or all of the features of the top region of FIG. 3b. In the illustrated embodiment, the top region 400 can include a top portion of the extendable structure 310, a top portion of the outer structure 220, an adjustment knob 404, and one or more connection point(s) 408. Embodiments are not limited in this context.

The connection point(s) 408 may be disposed on the top of the extendable structure 310. In some embodiments, the distance from the connection point(s) 408 to the support surface 206 may be adjustable by altering the distance that the extendable structure 310 extends above the top of the outer structure 220. The distance from the connection point(s) 408 to the support surface 206 may be set by tightening the adjustment knob 404. The adjustment knob 404 can include a threaded portion and may be received by a threaded hole in the outer structure 220. For example, tightening the adjustment knob 404 may cause the threaded portion of the adjustment knob 404 to apply pressure to the extendable structure, thereby locking the distance the extendable structure 310 extends above the top of the outer structure 220. It will be appreciated that while the illustrated embodiment of the extendable structure 310 employs an adjustment knob 404 to lock the extendable structure 310 in position, other mechanisms and arrangements can additionally or alternatively be implemented.

Each of the connection point(s) 404 may enable a piece of medical equipment to attach to the mounting structure 100. In one non-limiting example, a piece of medical equipment can be an intravenous (IV) fluid bag. In some embodiments, the connection point(s) 404 may utilize one or more of a spiral structure, a clamp, hook, or a clip to attach the container comprising fluid for administration to a user body. However, one having ordinary skill in the art will appreciate that the connection point(s) may be configured in a variety of arrangements. In some embodiments, connection point(s) 404 are not required to attach certain types of medical equipment.

In some embodiments, the height of the connection point(s) 408 relative to the support surface may be adjusted using a mechanical advantage. One or more of a lever, gear, or pulley may be used to reduce the force needed to lift a piece of medical equipment, such as a container comprising a fluid for administration to a user body, to the appropriate height. In some embodiments, the direction of force to lift the container comprising a fluid for administration to a user body may be reversed. For example, a user may push down on a lever to lift the container comprising a fluid for administration to a user body. In some embodiments, the top region 200 may include one or more electronic components such as a battery, a memory, a processor, a sensor, and an actuator.

In some embodiments, the top region may include a cord and/or tube management system (not shown). The cord and/or tube management system may provide routing, reduced clutter, and easy cord and/or tube tracing. The cord and/or tube management system may include one or more of a clip, spiral structure, "c", "s", or similar structure, cavities, and/or channels.

It will be appreciated by one having ordinary skill in the art that the top region arrangements described in FIG. 4 can be readily combined or modified. For example, one or more connection points 404 may be included on the outer structure 220 between the base end and the top end for attaching one or more types of medical equipment. In some embodiments, the components of the top region may be included in the base and middle regions with the mounting structure terminating at the top end of the outer structure 220.

Figure 5:
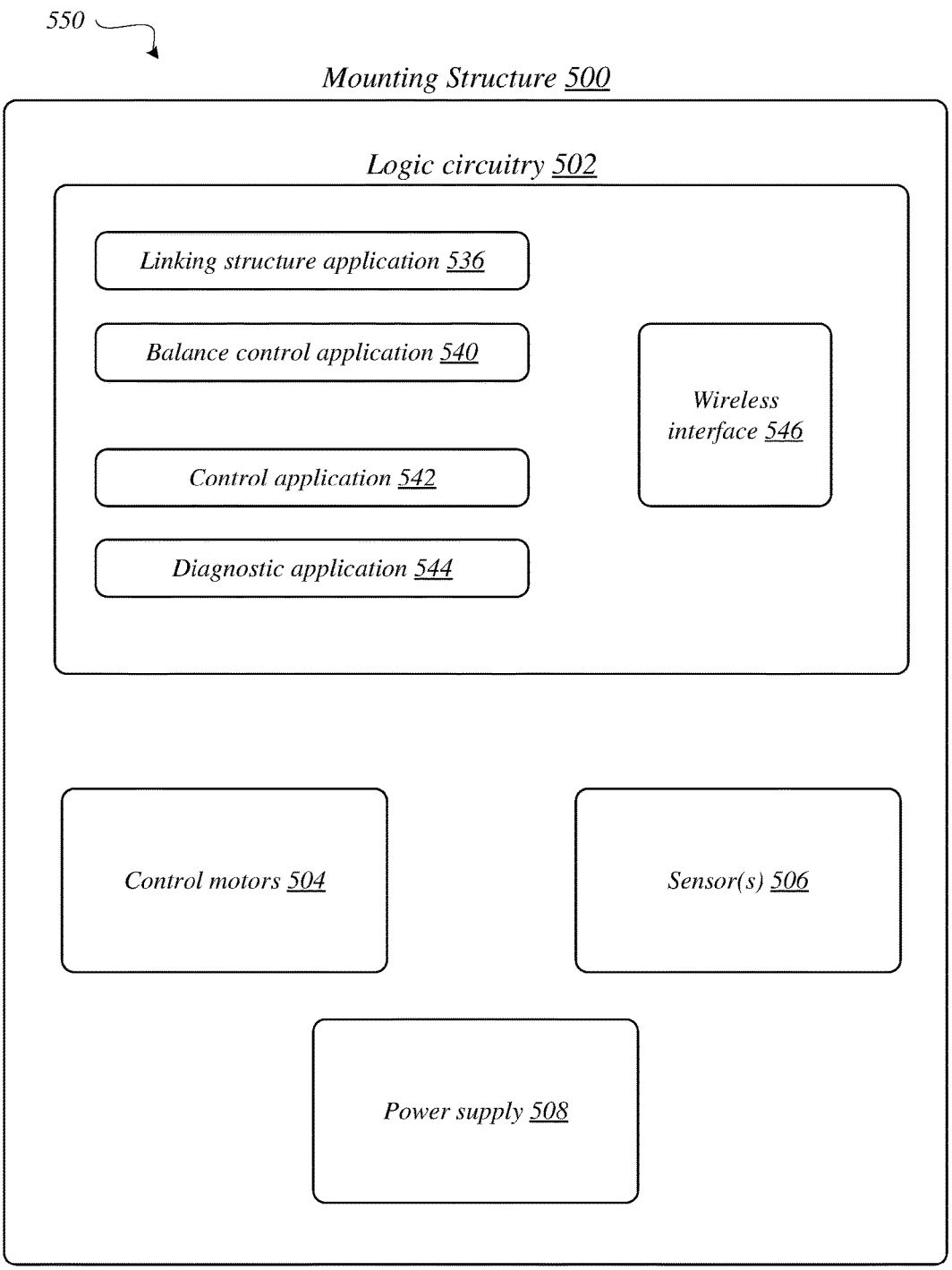
FIG. 5 is an exemplary embodiment of a mounting structure with logic circuitry.

FIG. 5 illustrates an embodiments of mounting structure 500 with logic circuitry 502. Mounting structure 500 may include logic circuitry 502, control motors 504, sensors 506, and power supply 508. Interoperation of these components can enable mounting structure 500 to improve functionality and increase patient safety. In various embodiments, mounting structure 500 includes one or more features or components of mounting structure 100. Embodiments are not limited in this context.

Logic circuitry 502 may utilize one or more applications to implement one or more functional aspects of mounting structure 500. In various embodiments, these functional aspects include one or more features described herein. In some embodiments, logic circuitry 502 may include one or more of processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, logic circuitry receives power from power supply 508.

Control motors 504 may include one or more physical for generators such as an actuator or an electric motor. In some embodiments control motor 504 may include a hydraulic motor. In various embodiments at least one of control motors 504 may activate a braking mechanism. In various such embodiments the braking mechanism may be activated in response to a control signal from an application (e.g., 536, 540, 542, 544) to one or more of control motors 504. In some embodiments control motors 504 may cause mounting structure 500 to move. For example, one or more of control motors 504 may drive the mounting structure 500 along a support surface (e.g., selectively rotate one or more of support surface interfaces 204). In some embodiments the drive motor may also comprise the braking mechanism.

Sensors 506 may include one or more transducers to convert a physical quantity into a digital signal. In some embodiments data from sensors 506 may be utilized by applications of logic circuitry 502 to implement one or more function aspects of mounting structure 500, such as control motors 504, for instance. In various embodiments sensors 506 include one or more of a gyroscope, global positioning system (GPS), voltage, mechanical position, electromagnetic wave, inertial, or similar sensor. In various embodiments, one or more sensors 506 may be remote to mounting structure 500. In various such embodiments, the one or more sensors 506 may be attached to a user. Such remote sensors would be able to communicate with logic circuitry 502. In some embodiments, a sensor may monitor the level of a tank of compressed gas.

Power supply 508 may provide electrical energy necessary to operate mounting structure 500. In some embodiments a direct current (DC) power may be provided. In various embodiments, power supply 508 may include a battery, such as a rechargeable electrochemical battery. Status of power supply 508 may be monitored by logic circuitry 502 (e.g. via 542 and/or 544).

In the illustrated embodiment, logic circuitry 502 includes linking structure application 536, balance control application 540, control application 542, and diagnostic application 544, and wireless interface 546. In various embodiments, applications of logic circuitry 502 may communicate with one or more of the control motors 504, sensors 506, and power supply 508. In various such embodiments, the communication may be achieved via one or more buses. Applications may function independent or dependently to achieve functional aspects described and disclosed herein. Applications 536, 540, 542, 544 are provided as an example embodiments, however, different or additional applications may be utilized in other embodiments to achieve the same or different functional aspects without departing from the scope of this disclosure.

In various embodiments, linking structure application 536 may receive data via one or more of sensors 506. The data may indicate a position of a switch. In some embodiments, the switch comprises an input surface (e.g., input surface 304). The switch may receive input from a user. This input may indicate that the coefficient of friction between the mounting structure 500 and a support surface should be altered. In some embodiments, based on the position of the switch, linking structure application 536 may activate a braking mechanism via one or more of control motors 504. This can provide an efficient and reliable way to improve patient safety. For example, when a patient needs balance support, linking structure application 536 may receive input via one or more of sensors 506 and, in response, cause mounting structure 500 to act as a stable support. In some embodiments, one or more of sensors 506 may be remote to mounting structure 500. In these embodiments, wireless interface 546 may facilitate communication.

In some embodiments, balance control application 540 may receive position or orientation data from one or more of sensors 506. Based on this data, balance control application 540 may direct linking structure application 536 to cause a braking mechanism (e.g. activated by one or more of control motors 504) to alter the coefficient of friction between mounting structure 500 and a support surface (e.g. 206). In some embodiments, based on the data, balance control application 540 may direct control motors 504 to maintain a specific position and/or orientation of mounting structure 500. In various embodiments, this may be achieved by continually comparing position/orientation data to a target position/orientation and powering one or more control motors 504 based on the comparison. For instance, proper orientation of mounting structure 500 may include an inverted pendulum orientation. In another example, proper orientation of mounting structure 500 may include a pendulum orientation. To this end, in some embodiments, a proportional integral derivative (PID) controller may be used. In some embodiments, balance control application 540 utilizes one or more of sensors 506 to monitor a coefficient of friction between mounting structure 500 and a support surface. In various embodiments, balance control application 540 monitors a ground speed of mounting structure 500. In various such embodiments, when the ground speed exceeds a predetermined amount, the coefficient of friction between the mounting structure 500 and a support surface can be increased. In some embodiments, this may also be a factor of acceleration of mounting structure 500. In some embodiments, acceleration of mounting structure 500 may be monitored at multiple positions on mounting structure 500.

In various embodiments control application 542, may monitor one or more aspects of mounting structure 500. For example, control application 542 may monitor application of a therapy (e.g., medication) via one or more of sensors 506. In various embodiments, control application 542 may enable a user to adjust one or more settings. In various such embodiments, control application 542 may cause a graphical user interface (GUI) to be displayed. The GUI may facilitate input/output (I/O) with a user. In some embodiments the user may adjust settings via a remote computer device. For example, control application 542 may utilize wireless interface 546 to receive I/O through a networked computer (e.g., over WIFI).

In some embodiment, diagnostic application 544 may monitor operational parameters of one or more features of mounting structure 500. The diagnostic application 544 may improve reliability on mounting structure 500. In various embodiments, diagnostic application 544, may monitor power supply 508. In various such embodiments diagnostic application 544 may provide a visual indication of charge of the power supply 508. In some embodiments, diagnostic application 544 may monitor the functionality of one or more components of mounting structure 500, such as, logic circuitry 502, control motors 504, sensors 506, or power supply 508.

Figure 6:
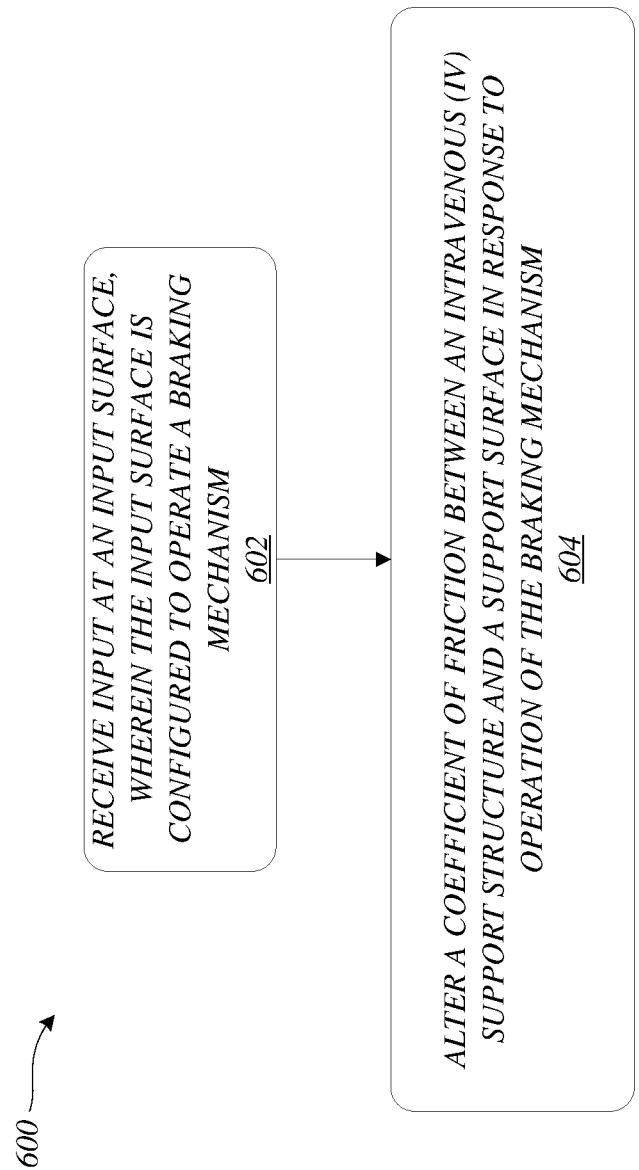
FIG. 6 is a logic diagram illustrating an exemplary method of providing support to a user in accordance with an embodiment of the present disclosure.

Referring now to FIG. 6, an exemplary method of providing support to a user will be described in greater detail. As shown in block 600, an input can be received by an input surface. In some embodiments, the input includes vertical displacement of the input surface. The input surface may be configured to operate a braking mechanism. In some embodiments, the input surface includes a handle. In one exemplary non-limiting embodiment, the input surface includes a handle receiver to serve as an attachment point for one or more styles of handle.

At step 604, the coefficient of friction between a mounting structure and a support surface can be altered in response to an operation of the braking mechanism. In some embodiments the mounting structure may include a base comprising three or more wheels. In certain embodiments the braking mechanism can be configured to alter the coefficient of friction between the mounting structure and the support surface by restricting a rotational movement of one or more wheels included in the base.

It will be appreciated by one having ordinary skill in the art that the method for providing support to a user described in FIG. 6 can be readily combined or modified by the embodiments and examples described herein.

One having ordinary skill in the art will appreciate that various attachment and/or connection devices described herein can readily be replaced with any known attachment or connection techniques such as welding, fusing, gluing, screwing, and other comparable techniques.

Referring again to the mounting structure 100, 500, electrical components included in the mounting structure 100, 500 can be configured in many arrangements. For example, the mounting structure 100, 500 can include one or more electrical outlets. The electrical outlets may be used to power a piece of medical equipment. In some embodiments, the power may be obtained from a battery included in the mounting structure 100, 500.

In one non-limiting embodiment, the electronic components may be configured to track and/or locate the approximate position and/or status of the mounting structure 100, 500. The status of the mounting structure 100 can include the status of any attached medical equipment. In some embodiments, an alarm may be triggered when a component of a piece of medical equipment attached to a user is about to become detached. For example, a user can receive IV fluids from a fluid container attached to the mounting structure 100, 500 and if the user moves away from the fluid container far enough to draw the tube connecting the user and the fluid container sufficiently tight, an alarm can sound to alert the user. In some embodiments, one or more components described herein may be used to retrofit an existing mounting structure. The one or more component may come in a kit that may be installed on an existing mounting structure.

FIG. 7 illustrates an embodiment of a storage medium 700. Storage medium 700 may comprise any non-transitory computer-readable storage medium or machine-readable storage medium, such as an optical, magnetic or semiconductor storage medium. In various embodiments, storage medium 700 may comprise an article of manufacture. In some embodiments, storage medium 700 may store computer-executable instructions, such as computer-executable instructions to implement one or more of logic flows 550, 600 of FIGS. 5-6. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited in this context.

Figure 8:
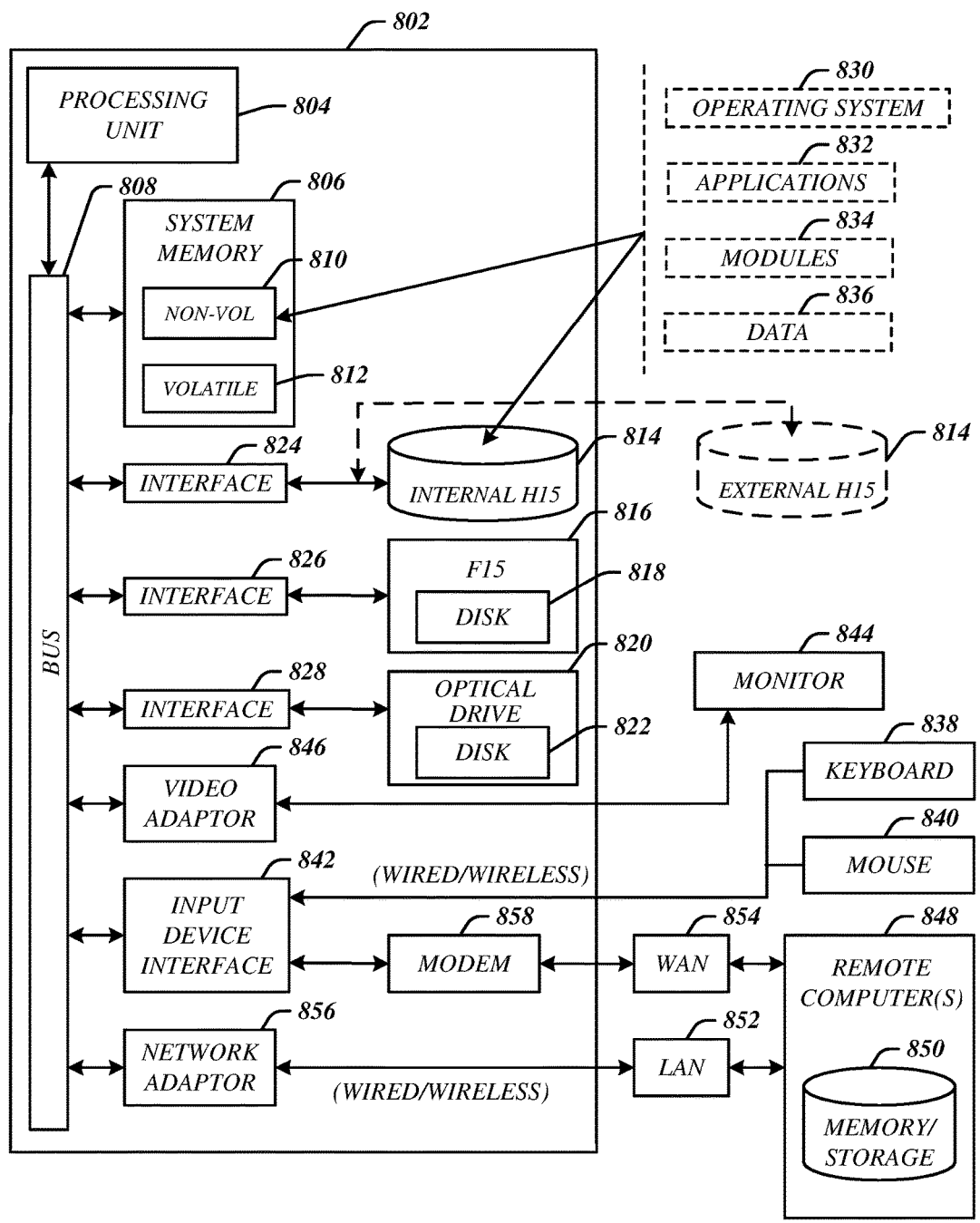
FIG. 8 illustrates an embodiment of a computing architecture.

FIG. 8 illustrates an embodiment of an exemplary computing architecture 800 that may be suitable for implementing various embodiments as previously described. In various embodiments, the computing architecture 800 may comprise or be implemented as part of an electronic device. In some embodiments, the computing architecture 800 may be representative, for example, of a processor server that implements one or more components of the mounting structure 100, 500. In some embodiments, computing architecture 900 may be representative, for example, of a terminal device that implements one or more components functionality of mounting structure 100, 500. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 800. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 800 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 800.

As shown in FIG. 8, the computing architecture 800 comprises a processing unit 804, a system memory 806 and a system bus 808. The processing unit 804 can be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 804.

The system bus 808 provides an interface for system components including, but not limited to, the system memory 806 to the processing unit 804. The system bus 808 can be any of several types of bus structure that may further interconnect to a memory bus (with or without a memory controller), a peripheral bus, and a local bus using any of a variety of commercially available bus architectures. Interface adapters may connect to the system bus 808 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 806 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 8, the system memory 806 can include non-volatile memory 810 and/or volatile memory 812. A basic input/output system (BIOS) can be stored in the non-volatile memory 810.

The computer 802 may include various types of computer-readable storage media in the form of one or more lower speed memory units, including an internal (or external) hard disk drive (HDD) 814, a magnetic floppy disk drive (FDD) 816 to read from or write to a removable magnetic disk 818, and an optical disk drive 820 to read from or write to a removable optical disk 822 (e.g., a CD-ROM or DVD). The HDD 814, FDD 816 and optical disk drive 820 can be connected to the system bus 808 by a HDD interface 824, an FDD interface 826 and an optical drive interface 828, respectively. The HDD interface 824 for external drive implementations can include at least one or both of Universal Serial Bus (USB) and IEEE 994 interface technologies.

The drives and associated computer-readable media provide volatile and/or nonvolatile storage of data, data structures, computer-executable instructions, and so forth. For example, a number of program modules can be stored in the drives and memory units 810, 812, including an operating system 830, one or more application programs 832, other program modules 834, and program data 836. In one embodiment, the one or more application programs 832, other program modules 834, and program data 836 can include, for example, the various applications and/or components of the embodiments described herein.

A user can enter commands and information into the computer 802 through one or more wire/wireless input devices, for example, a keyboard 838 and a pointing device, such as a mouse 840. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 804 through an input device interface 842 that is coupled to the system bus 808, but can be connected by other interfaces such as a parallel port, IEEE 884 serial port, a game port, a USB port, an IR interface, and so forth.

A monitor 844 or other type of display device is also connected to the system bus 808 via an interface, such as a video adaptor 846. The monitor 844 may be internal or external to the computer 802. In addition to the monitor 844, a computer typically includes other peripheral output devices, such as speakers, printers, and so forth.

The computer 802 may operate in a networked environment using logical connections via wire and/or wireless communications to one or more remote computers, such as a remote computer 848. The remote computer 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wire/wireless connectivity to a local area network (LAN) 852 and/or larger networks, for example, a wide area network (WAN) 854. Such LAN and WAN networking environments are commonplace in offices and companies, and facilitate enterprise-wide computer networks, such as intranets, all of which may connect to a global communications network, for example, the Internet.

When used in a LAN networking environment, the computer 802 is connected to the LAN 852 through a wire and/or wireless communication network interface or adaptor 856. The adaptor 856 can facilitate wire and/or wireless communications to the LAN 852, which may also include a wireless access point disposed thereon for communicating with the wireless functionality of the adaptor 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wire and/or wireless device, connects to the system bus 808 via the input device interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Figure 9:
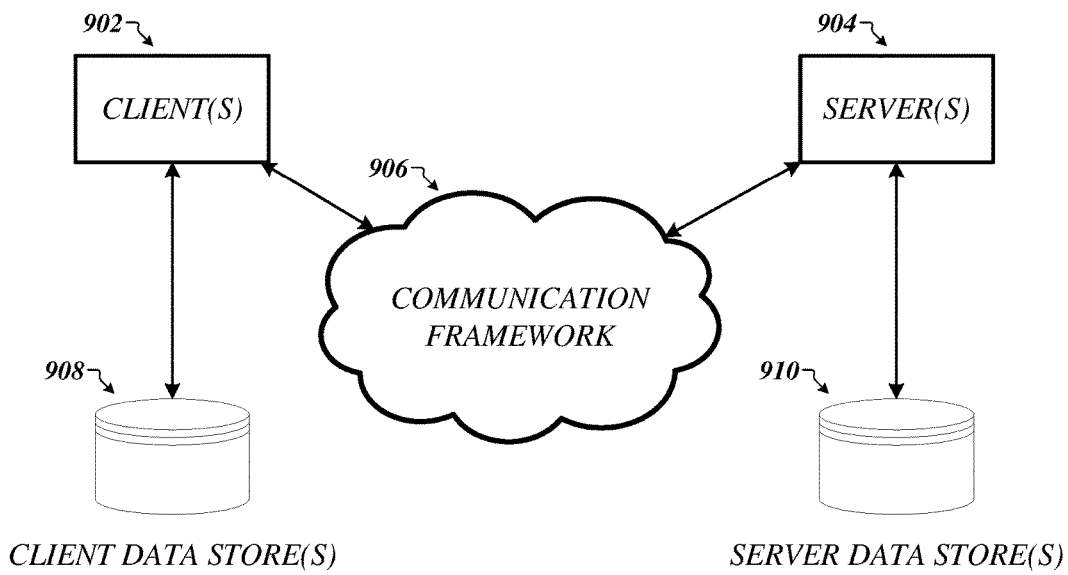
FIG. 9 illustrates an embodiment of a communications architecture.

FIG. 9 illustrates a block diagram of an exemplary communications architecture 1400 suitable for implementing various embodiments as previously described. The communications architecture 900 includes various common communications elements, such as a transmitter, receiver, transceiver, radio, network interface, baseband processor, antenna, amplifiers, filters, power supplies, and so forth. The embodiments, however, are not limited to implementation by the communications architecture 900.

As shown in FIG. 9, the communications architecture 900 comprises includes one or more clients 902 and servers 904. The clients 902 and the servers 904 are operatively connected to one or more respective client data stores 908 and server data stores 910 that can be employed to store information local to the respective clients 902 and servers 904, such as cookies and/or associated contextual information. In various embodiments, any one of servers 904 may implement one or more of logic flows 550-600 of FIGS. 5-6, and storage medium 700 of FIG. 7 in conjunction with storage of data received from any one of clients 902 on any of server data stores 910.

The clients 902 and the servers 904 may communicate information between each other using a communication framework 906. The communications framework 906 may implement any well-known communications techniques and protocols. The communications framework 906 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 906 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1900 Base T, and the like), token ring, wireless network interfaces, cellular network interfaces, IEEE 802.11a-x network interfaces, IEEE 802.16 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 902 and the servers 904. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Thus, the present disclosure provides mounting structures and methods for providing support. An advantage, offered by the structures and methods of the present disclosure is that they can provide support to a user. Another advantage offered by the structures and methods of the present disclosure is that they provide increase safety by enabling a user to regain their balance. A third main advantage offered by the structures and methods of the present disclosure is that they can enable a user to avoid injuries.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure.

Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A mounting structure comprising:
   a connection point to couple with an intravenous (IV) fluid container;
   a base to facilitate movement of the mounting structure relative to a support surface;
   a braking mechanism operable to cause the mounting structure to resist movement relative to the support surface; and
   an input surface to receive an input force the input force to cause the braking mechanism to activate, thereby causing the mounting structure to resist movement relative to the support surface by causing a braking surface to contact the support surface, wherein the input force to activate the braking mechanism is selectively adjustable and a distance of the input surface relative to the support surface is selectively adjustable.

2. The mounting structure of claim 1, the input surface located at least 18 inches from the base.

3. The mounting structure of claim 1, wherein at least as portion of the input surface encircles the mounting structure.

4. The mounting structure of claim 1, the braking mechanism mechanically linked to the input surface.

5. A method for providing support to a user, comprising:
adjusting an input force required to activate a braking mechanism of a mounting structure, the mounting structure comprising the braking mechanism, an input surface to receive the input force required to activate the braking mechanism, a base to facilitate movement of mounting structure relative to a support surface, and a connection point to couple to an intravenous (IV) fluid container;
receiving the input force at the input surface, to operate the braking mechanism; and
altering a coefficient of friction between the mounting structure and the support surface in response to operation of the braking mechanism with the input force to activate the braking mechanism, wherein altering the coefficient of friction includes causing at least a portion of the braking mechanism to contact the support surface.

6. The method of claim 5, the input surface comprising a handle.

7. The method of claim 6, receiving the input force at the input surface to cause a vertical displacement of the handle.

8. The method of claim 5, the input surface comprising a handle receiver, the handle receiver to serve as an attachment point for one or more styles of handle.

9. The method of claim 5, the base comprising three or more wheels, wherein the three or more wheels are configured to displace upon application of a lateral force to the mounting structure.

10. An apparatus, comprising:
a connection point to couple with an intravenous (IV) fluid container;
a base comprising one or more wheels to facilitate movement of a mounting structure relative to a support surface;
a braking mechanism activatable to cause the mounting structure to resist movement relative to the support surface in response to an input force, the braking mechanism comprising a braking surface to contact the support surface and cause the mounting structure to resist movement relative to the support surface in response to the input force, wherein the input force to activate the braking mechanism is selectively adjustable; and
an input surface linked to the braking mechanism, the input surface to receive the input force to cause the braking mechanism to activate, thereby causing the mounting structure to resist movement relative to the support surface.

11. The apparatus of claim 10, wherein a distance of the input surface relative to the base is selectively adjustable.

12. The apparatus of claim 10, comprising a sensor and processing circuitry, the processing circuitry to detect the input force via the sensor and cause the braking mechanism to activate in response to detection of the input force via the sensor.

13. The apparatus of claim 10, wherein the braking mechanism is mechanically linked to the input surface.

14. The apparatus of claim 10, comprising a plurality of connection points to attach medical equipment.

15. The apparatus of claim 10, wherein the input surface encircles at least a portion of the mounting structure.

16. The apparatus of claim 14, comprising a tube management system to retain tubing associated with the medical equipment.

17. The apparatus of claim 14, the medical equipment comprising one or more of a pump, diagnostic equipment, and monitoring equipment.

18. The apparatus of claim 10, the input force to cause the braking mechanism to activate comprising a downward force toward the base.

19. The apparatus of claim 10, wherein the input force to activate the braking mechanism is selectively adjustable via adjustment of an effective spring constant.

20. The apparatus of claim 10, the input surface comprising a handle receiver, the handle receiver to serve as an attachment point for one or more styles of handle.

* * * * *